United States Patent [19]

Carling et al.

[11] Patent Number: 5,475,008

[45] Date of Patent: Dec. 12, 1995

[54] QUINOLONE DERIVATIVES

[75] Inventors: William R. Carling, Bishops Stortford; Paul D. Leeson, Cambridge; Michael Rowley, Harlow, all of Great Britain

[73] Assignee: Merck Sharp & Dohme Limited, Hoddesdon, England

[21] Appl. No.: 244,310

[22] PCT Filed: Nov. 25, 1992

[86] PCT No.: PCT/GB92/02182

§ 371 Date: May 25, 1994

§ 102(e) Date: May 25, 1994

[87] PCT Pub. No.: WO93/10783

PCT Pub. Date: Jun. 10, 1993

[30] Foreign Application Priority Data

Nov. 29, 1991 [GB] United Kingdom .................. 9125485

[51] Int. Cl.⁶ .................. C07D 215/227; C07D 215/18; C07D 215/38
[52] U.S. Cl. .................. 514/312; 546/156; 546/157
[58] Field of Search .................. 546/157, 156; 514/312

[56] References Cited

U.S. PATENT DOCUMENTS 4,284,768  8/1981  Santilli .................. 544/128
4,902,695  2/1990  Ornstein .................. 514/307
5,371,226  12/1994  Mederski .................. 546/156

FOREIGN PATENT DOCUMENTS

0120483A1  3/1984  European Pat. Off. ..
0303387A1  8/1988  European Pat. Off. ..

OTHER PUBLICATIONS

G. Cavicchio, "Oxygen Heterocycles by Sulphur Ylide Annulation . . . ", Gazzetta Chimica Italiana, 119, pp. 367–373, 1989.

Chemical Abstracts, 99: 79987c, 1983.

Primary Examiner—C. Warren Ivy
Assistant Examiner—D. Margaret M. Mach
Attorney, Agent, or Firm—Robert J. North; Melvin Winokur

[57] ABSTRACT

A class of 2(1H)-quinolone derivatives, substituted at the 3-position by a range of carbonyl-containing substituents or by a five- or six-membered heteroaromatic moiety, are selective non-competitive antagonists of NMDA receptors and/or are antagonists of AMPA receptors, and are therefore of utility in the treatment of conditions, such as neurodegenerative disorders, convulsions or schizophrenia, which require the administration of an NMDA and/or AMPA receptor antagonist.

8 Claims, No Drawings

QUINOLONE DERIVATIVES

This application is a 371 of PCT/GB92/02182, filed 25 Nov. 1994, now WO 93/10783.

This invention relates to a particular class of 2(1H)-quinolone derivatives which are selective non-competitive antagonists of N-methyl-D-aspartate (NMDA) receptors. More particularly, the class of compounds provided by the present invention are ligands for the strychnine-insensitive glycine modulatory site of the NMDA receptor and are therefore useful in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by exogenous and endogenous NMDA receptor agonists and neurotoxins, including environmental neurotoxins.

By virtue of their NMDA receptor antagonist properties, the compounds according to the present invention are also useful as anticonvulsant and antiemetic agents, as well as being of value in the prevention or reduction of dependence on dependence-inducing agents such as narcotics.

NMDA receptor antagonists have recently been shown to possess analgesic (see, for example, Dickenson and Aydar, *Neuroscience Lett.*, 1991, 121, 263; Murray et al., *Pain*, 1991, 44, 179; and Woolf and Thompson, *Pain*, 1991, 44, 293) and anxiolytic (see, for example, U.S. Pat. No. 5,145,866; and Kehne et al., *Eur. J. Pharmacol.*, 1991, 193,283) effects, and the compounds of the present invention may accordingly be useful in the management of pain and anxiety.

Compounds possessing functional antagonist properties for the NMDA receptor complex are stated in WO-A-91/19493 to be effective in the treatment of mood disorders, including major depression, bipolar disorder, dysthymia and seasonal affective disorder (cf. also Trullas and Skolnick, *Eur. J. Pharmacol.*, 1990, 185, 1). The compounds of the present invention may consequently be of benefit in the treatment and/or prevention of such disorders.

The association of NMDA receptor antagonists with regulation of the dopaminergic system has recently been reported (see, for example, Werling et al., *J. Pharmacol. Exp. Ther.*, 1990, 255, 40; Graham et al., *Life Sciences*, 1990, 47, PL-41; Hutson et al., *Br. J. Pharmacol.*, 1991, 103, 2037; and Turski et al., *Nature (London)*, 1991, 349, 414). This suggests that the compounds of the present invention may thus be of assistance in the prevention and/or treatment of disorders of the dopaminergic system such as schizophrenia and Parkinson's disease.

It has also been reported recently (see Lauritzen et al., *Journal of Cerebral Blood Flow and Metabolism*, 1991, vol. 11, suppl. 2, Abstract XV-4) that NMDA receptor antagonists block cortical spreading depression (CSD), which may thus be of clinical importance since CSD is a possible mechanism of migraine. The class of substituted 2-amino-4-phosphonomethylalk-3-ene carboxylic acids and esters described in EP-A-0420806, which are stated to be selective NMDA antagonists, are alleged thereby to be of potential utility in the treatment of inter alia migraine.

Excitatory amino acid receptor antagonists, including inter alia antagonists of NMDA receptors, are alleged in EP-A-0432994 to be of use in suppressing emesis.

Recent reports in the literature have also suggested a link between the neurotoxicity of certain viruses and the deleterious effects of these viruses on an organism caused by the potentiation of neurotransmission via excitatory amino acid receptors. By virtue of their activity as antagonists of NMDA receptors, therefore, the compounds of the present invention may be effective in controlling the manifestations of neuroviral diseases such as measles, rabies, tetanus (cf. Bagetta et al., *Br. J. Pharmacol.*, 1990, 101, 776) and AIDS (cf. Lipton et al., *Society for Neuroscience Abstracts*, 1990, 16, 128.11).

NMDA antagonists have, moreover, been shown to have an effect on the neuroendocrine system (see, for example, van den Pol et al., *Science*, 1990, 250, 1276; and Urbanski, *Endocrinology*, 1990, 127, 2223), and the compounds of this invention may therefore also be effective in the control of seasonal breeding in mammals.

In addition, certain compounds of the invention are antagonists of 2-amino-3-hydroxy-5-methyl-4-isoxazolepropionic acid (AMPA) receptors, also known as quisqualate receptors. An excitatory amino acid projection from the prefrontal cortex to the nucleus accumbens (a particular region of the forebrain possessing dopamine-sensitive neurones) is well known to exist (see, for example, *J. Neurochem.*, 1985, 45, 477). It is also well known that dopaminergic transmission in the striatum is modulated by glutamate (see, for example, *Neurochem. Int.*, 1983, J, 479), as also is the hyperactivity associated with presynaptic stimulation of the dopamine system by AMPA in the nucleus accumbens (cf. *Life Sci.*, 1981, 28, 1597). Compounds which are antagonists of AMPA receptors are therefore of value as neuroleptic agents.

The compound 4-amino-3-methoxycarbonyl-6-nitro-2(1H)-quinolone is disclosed in *Tetrahedron Lett.*, 1990, 31, 3485, although no therapeutic utility is mentioned therein for this compound.

A class of 2(1H)-quinolone-3-carboxylic acid derivatives, substituted at the 4-position by an optionally substituted amino group, is described in U.S. Pat. No. 4284768. These compounds are alleged to be gastric anti-secretory agents, and thus useful in the treatment of peptic ulcer disease. The compound 4-amino-6-chloro- 3-ethoxycarbonyl-2-(1H)-quinolone is specifically disclosed in U.S. Pat. No. 4,284,768.

A family of 2(1H)-quinolone derivatives, substituted inter alia at the 3-position by a 1H-tetrazol- 5-yl group, is described in EP-A-0120483. These compounds are stated to be useful as antiallergic agents.

Nowhere in U.S. Pat. No. 4,284,768 or EP-A-0120483 is there any suggestion that the compounds described therein would be of assistance in solving the problem of providing an effective agent for the treatment and/or prevention of conditions requiring the administration of an antagonist of NMDA and/or AMPA receptors.

The present invention accordingly provides the use of a compound of formula I or a pharmaceutically acceptable salt thereof or a prodrug thereof:

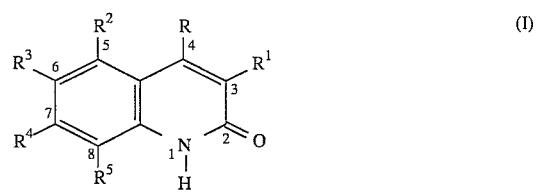

wherein

R represents a hydrogen atom, an amino group, a carboxy or $C_{2-6}$ alkoxycarbonyl group, or a group of formula -α-β-ε, in which α represents a chemical bond, an oxygen or sulphur atom, or an —NH— group;

β represents a carbonyl (C=O) or sulphonyl (SO$_2$) group, or a straight or branched alkylene chain containing from 1 to 6 carbon atoms; and ε represents C$_{1-6}$ alkyl, C$_{2-6}$ alkenyl, phenyl, —NR$^a$R$^b$, —CO$_2$R$^a$ or —CH$_2$CO$_2$R$^a$;

R$^1$ is a group of part formula (i) or (ii):

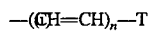

—(CH=CH)$_n$—T

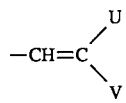

$$-CH=C\diagup_V^U \quad (ii)$$

wherein

U and V independently represent cyano, carboxy, —COR$^6$, —CO$_2$R$^6$, —CO.SR$^6$, —CONHOH or —CONHNH$_2$;

n is zero or 1, preferably zero;

T represents cyano, carboxy, —COR$^6$, —CO$_2$R$^6$, —CO.SR$^6$, —CONHOH, —CONHNH$_2$ or a group of formula

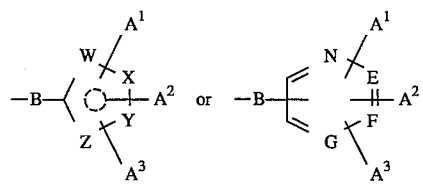

in which the broken circle represents two non-adjacent double bonds in any position in the five-membered ring;

B represents a bond or a carbonyl group (C=O);

W, X, Y and Z independently represent oxygen, sulphur, nitrogen or carbon, provided that no more than one of W, X, Y and Z represents oxygen or sulphur and at least one of W, X, Y and Z is other than carbon;

one of E, F and G represents nitrogen or carbon and the remainder represent carbon;

A$^1$ A$^2$ and A$^3$ represent one, two or three substituents not exceeding the maximum number permissible by the disposition of heteroatoms in the five- or six-membered ring, which substituents are independently selected from hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$COR$^b$, —COR$^a$, —CO$_2$R$^a$ or —CONR$^a$R$^b$; or A$^1$ and A$^2$ or A$^2$ and A$^3$ together represent the residue of an aromatic or heteroaromatic ring;

one of R$^2$, R$^3$, R$^4$ and R$^5$ represents hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$ and the other three of R$^2$, R$^3$, R$^4$ and R$^5$ independently represent hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, NR$^a$CO$_2$R$^b$, —COR$^a$, —CO$^2$R$^a$ or —CONR$^a$R$^b$; or R$^2$ and R$^3$, R$^3$ and R$^4$ or R$^4$ and R$^5$ together represent the residue of an aromatic or heteroaromatic ring;

R$^6$ represents hydrocarbon or a heterocyclic group; and

R$^a$ and R$^b$ independently represent hydrogen, hydrocarbon or a heterocyclic group;

for the manufacture of a medicament for the treatment and/or prevention of conditions, in particular neurodegenerative disorders, which require the administration of a selective non-competitive antagonist of NMDA receptors.

The present invention further provides the use of a compound of formula I as defined above or a pharmaceutically acceptable salt thereof or a prodrug thereof for the manufacture of a medicament for the treatment and/or prevention of conditions, such as schizophrenia, which require the administration of an antagonist of AMPA receptors.

The compounds of formula I can exist as alternative tautomeric forms. It is to be understood that all tautomeric forms of the compounds of formula I, as well as all possible mixtures thereof, are included within the scope of the present invention.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C1-6)alkyl, aryl, aryl(C$_{1-6}$)alkyl, aryl(C$_{2-6}$)alkenyl and aryl(C$_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$)alkyl.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups. Particular aryl(C$_{1-6}$)alkyl groups include benzyl, phenethyl, phenylpropyl and phenylbutyl.

A particular aryl(C$_{2-6}$)alkenyl group is phenylallyl.

A particular aryl(C$_{2-6}$)alkynyl group is phenylpropargyl.

Suitable heterocycloalkyl groups include piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, thienyl, benzthienyl, pyrrolyl, indolyl, imidazolyl, oxadiazolyl and thiadiazolyl groups. Particular heteroaryl groups are pyridyl, furyl, benzofuryl, thienyl, benzthienyl, pyrrolyl, indolyl and oxadiazolyl.

Particular heteroaryl(C$_{1-6}$)alkyl groups include indolylethyl, indolylpropyl and thienylethyl. The hydrocarbon and heterocyclic groups may in turn be optionally substituted by one or more groups selected from C$_{1-6}$ alkyl, adamantyl, phenyl, halogen, C$_{1-6}$ haloalkyl, trifluoromethyl, hydroxy, C$_{1-6}$ alkoxy, alkoxy (C$_{1-6}$) alkoxy, aryloxy, keto, C$_{1-3}$ alkylenedioxy, nitro, cyano, carboxy, $C_{2-6}$ alkoxycarbonyl, alkoxycarbonyl ($C_{1-6}$) alkyl, $C_{2-6}$ alkylcarbonyloxy, optionally substituted arylcarbonyloxy, alkylcarbonyl, optionally substituted arylcarbonyl, alkylthio, $C_{1-6}$ alkylsulphinyl, $C_{1-6}$ alkylsulphonyl, arylthio, amino, mono- or di ($C_{1-6}$) alkylamino, $C_{2-6}$ alkylcarbonylamino, $C_{2-6}$ alkoxycarbonylamino and $C_{2-6}$ alkoxycarbonylamino ($C_{1-6}$) alkyl.

The term "halogen" as used herein includes fluorine, chlorine, bromine and iodine, especially chlorine.

When R in the compounds of formula I above represents a group of formula -α-β-ε, and β represents a straight or branched alkylene chain containing from 1 to 6 carbon atoms, this alkylene chain may be, for example, methylene, ethylene, 1-methylethylene, propylene or 2-methylpropylene, preferably methylene, ethylene or propylene.

Examples of suitable substituents represented by the group R include hydrogen, carboxy($C_{1-6}$)alkoxy, $C_{2-6}$ alkoxycarbonyl($C_{1-6}$)alkoxy, $C_{3-10}$ alkenyloxy, amino, phenyl ($C_{1-6}$) alkylamino, amino ($C_{1-6}$) alkylamino, di ($C_{1-6}$) alkylamino ($C_{1-6}$) alkylamino, carboxy ($C_{1-6}$) alkylamino, $C_{2-6}$ alkanoylamino, carboxy-carbonylamino, $C_{2-6}$ alkoxycarbonyl-carbonylamino, carboxymethylcarbonylamino, $C_{2-6}$ alkoxycarbonylmethyl-carbonylamino, $C_{1-6}$ alkylsulphonylamino, phenylsulphonylamino, carboxy, $C_{2-6}$ alkoxycarbonyl, carboxy($C_{1-6}$)alkyl and $C_{2-6}$ alkoxycarbonyl($C_{1-6}$)alkyl.

Particular examples of the substituent R include hydrogen, carboxy-methoxy, methoxycarbonylmethoxy, allyloxy, amino, benzylamino, dimethylaminoethylamino, dimethylamino-propylamino, acetylamino, carboxymethyl-carbonylamino, carboxy-carbonylamino, methoxycarbonyl-carbonylamino, methylsulphonylamino, phenylsulphonylamino, carboxy, methoxycarbonyl, carboxymethyl and methoxycarbonyl-methyl, especially hydrogen and amino.

The five-membered heteroaromatic ring containing the ring atoms W to Z may be, for example, a furan, thiophene, pyrrole, oxazole, thiazole, isoxazole, isothiazole, imidazole, oxadiazole, thiadiazole, triazole or tetrazole ring, in particular a furan, thiophene, pyrrole, 1,2,4-oxadiazole, 1,3,4-oxadiazole, 1,2,4-thiadiazole, 1,3,4-thiadiazole or tetrazole ring. Preferably the ring is a furan, thiophene, pyrrole, 1,2,4-oxadiazole, 1,2,4-thiadiazole or tetrazole ring.

The six-membered heteroaromatic ring containing the ring atoms E, F and G is a pyridine, pyrazine, pyrimidine or pyridazine ring, preferably pyridine or pyrazine. In the case of a pyridine ring, E, F and G each represents carbon. In the case of a pyrazine ring, for example, G represents nitrogen, and E and F each represents carbon.

The number of substituents $A^1$, $A^2$ and/or $A^3$ present on the five- or six-membered heteroaromatic ring containing the ring atoms W to Z or E to G respectively is one, two or three depending upon the disposition of heteroatoms in the heteroaromatic ring concerned. Thus where, for example, the five-membered heteroaromatic ring is an oxadiazole, thiadiazole or tetrazole ring, only one substituent will be permitted; where, for example, the five-membered heteroaromatic ring is an oxazole or thiazole ring, one or two substituents will be permitted; and where, for example, the five-membered heteroaromatic ring is a furan, thiophene or pyrrole ring, one, two or three substituents will be permitted. Where the heteroaromatic ring is a six-membered ring containing the ring atoms E, F and G it will be appreciated that one, two or three substituents $A^1$, $A^2$ and/or $A^3$ will be permitted.

Suitable values for the groups $A^1$, $A^2$ and/or $A^3$ include hydrogen, $C_{1-6}$ alkyl, $C_{2-6}$ alkenyl, $C_{2-6}$ alkynyl, $C_{3-7}$ cycloalkyl, $C_{3-7}$ cycloalkyl ($C_{1-6}$) alkyl, optionally substituted aryl, optionally substituted aryl ($C_{1-6}$) alkyl, halogen, cyano, trifluoromethyl, nitro, $C_{1-6}$ alkoxy, $C_{2-6}$ alkenyloxy, $C_{1-6}$ alkylthio, $C_{2-6}$ alkenylthio, —$COR^a$ or —$NR^aR^b$, in which $R^a$ and $R^b$ are as defined above.

When T, U or V represents a group of formula —$COR^6$, —$CO_2R^6$ or —$CO.SR^6$, the substituent $R^6$ suitably represents $C_{1-6}$ alkyl, $C_{2-6}$ alkenyl, $C_{2-6}$ alkynyl, $C_{3-7}$ cycloalkyl, $C_{3-7}$ cycloalkyl ($C_{1-6}$) alkyl, aryl, aryl-($C_{1-6}$) alkyl, aryl ($C_{2-6}$) alkenyl, aryl ($C_{1-6}$) alkynyl, $C_{3-7}$ heterocycloalkyl ($C_{1-6}$) alkyl, heteroaryl, heteroaryl-($C_{1-6}$)alkyl or heteroaryl ($C_{2-6}$) alkenyl, any of which groups may be optionally substituted.

The benzo moiety of the 2(1H)-quinolone ring system shown in formula I above contains at least one non-hydrogen substituent. Particular substituents include halogen, cyano, trifluoromethyl, nitro, hydroxy, amino, carboxy, $C_{1-6}$ alkyl, $C_{1-6}$ alkoxy, $C_{1-6}$ alkylthio and $C_{2-6}$ alkoxycarbonyl. Suitably, $R^5$ represents hydrogen and $R^2$, $R^3$ and $R^4$ independently represent hydrogen, halogen, nitro, amino or $C_{1-6}$ alkyl, provided that at least one of $R^2$, $R^3$ and $R^4$ is other than hydrogen. Preferably $R^3$ and $R^5$ each represents hydrogen and $R^2$ and $R^4$ independently represent hydrogen, nitro, amino, methyl or halogen, especially chlorine, provided that at least one of $R^2$ and $R^4$ is other than hydrogen. In a preferred embodiment, $R^4$ represents chlorine.

Where $R^2$ and $R^3$, $R^3$ and $R^4$, $R^4$ and $R^5$, $A^1$ and $A^2$ or $A^2$ and $A^3$ represent the residue of an aromatic or heteroaromatic ring, this is suitably an optionally substituted benzene, pyridine, thiophene, thiazole or thiadiazole ring. As optional substituents on the aromatic or heteroaromatic ring may be mentioned nitro, and $C_{1-6}$ alkoxy such as methoxy.

In a further aspect the present invention provides a pharmaceutical composition comprising a compound of formula IA or a pharmaceutically acceptable salt thereof or a prodrug thereof:

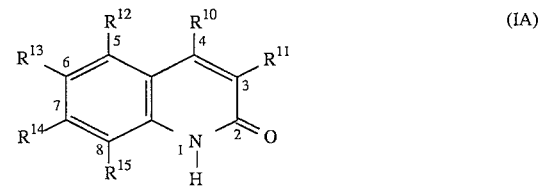

wherein $R^{10}$ represents a hydrogen atom, an amino group, a carboxy or $C_{2-6}$ alkoxycarbonyl group, or a group of formula -α-β-ε, in which α represents a chemical bond, an oxygen or sulphur atom, or an —NH— group;

β represents a carbonyl (C=O) or sulphonyl ($SO_2$) group, or a straight or branched alkylene chain containing from 1 to 6 carbon atoms; and ε represents $C_{1-6}$ alkyl, $C_{2-6}$ alkenyl, phenyl, —$NR^aR^b$, —$CO_2R^a$ or —$CH_2CO_2R^a$;

$R^{11}$ is a group of part formula (i) or (ii):

—(CH=CH)$_n$—T

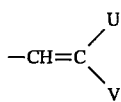

wherein

U and V independently represent cyano, carboxy, —COR⁶, —CO₂R⁶, —CO.SR⁶, —CONHOH or —CONHNH₂;

n is zero or 1, preferably zero;

T represents cyano, carboxy, —COR⁶, —CO₂R⁶, —CO.SR⁶, —CONHOH, —CONHNH₂ or a group of formula

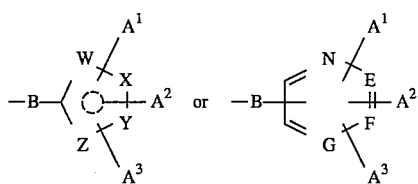

in which the broken circle represents two non-adjacent double bonds in any position in the five-membered ring;

B represents a bond or a carbonyl group (C=O);

W, X, Y and Z independently represent oxygen, sulphur, nitrogen or carbon, provided that no more than one of W, X, Y and Z represents oxygen or sulphur and at least one of W, X, Y and Z is other than carbon;

one of E, F and G represents nitrogen or carbon and the remainder represent carbon;

A¹, A² and A³ represent one, two or three substituents not exceeding the maximum number permissible by the disposition of heteroatoms in the five- or six-membered ring, which substituents are independently selected from hydrogen, hydrocarbon, a heterocyclic group, halogen, cyano, trifluoromethyl, nitro, —OR$^a$, —SR$^a$, —SOR$^a$, —SO₂R$^a$, —SO₂NR$^a$R$^b$, —NR$^a$R$^b$, —NR$^a$COR$^b$, —NR$^a$CO₂R$^b$, —COR$^a$, —CO₂R$^a$ or —CONR$^a$R$^b$; or A¹ and A² or A² and A³ together represent the residue of an aromatic or heteroaromatic ring;

one of R¹², R¹³, R¹⁴ and R¹⁵ represents hydrocarbon, a heterocyclic group, halogen, cyano, trifluoromethyl, nitro, —OR$^a$, —SR$^a$, —SOR$^a$, —SO₂R$^a$, —SO₂NR$^a$R$^b$, —NR$^a$R$^b$, —NR$^a$COR$^b$, —NR$^a$CO₂R$^b$, —COR$^a$, —CO₂R$^a$ or —CONR$^a$R$^b$, and the other three of R¹², R¹³, R¹⁴ and R¹⁵ independently represent hydrogen, hydrocarbon, a heterocyclic group, halogen, cyano, trifluoromethyl, nitro, —OR$^a$, —SR$^a$, —SOR$^a$, —SO₂R$^a$, —SO₂NR$^a$R$^b$, —NR$^a$R$^b$, —NR$^a$COR$^b$, —NR$^a$CO₂R$^b$, —COR$^a$, —CO₂R$^a$ or —CONR$^a$R$^b$; or R¹² and R¹³, R¹³ and R¹⁴ or R¹⁴ and R¹⁵ together represent the residue of an aromatic or heteroaromatic ring;

R⁶ represents hydrocarbon or a heterocyclic group; and

R$^a$ and R$^b$ independently represent hydrogen, hydrocarbon or a heterocyclic group;

provided that, when R¹¹ represents carboxy or C₂₋₇ alkoxycarbonyl, one of the substituents R¹² to R¹⁵ represents chloro or bromo and the other three substituents R¹² to R¹⁵ are hydrogen, then R¹⁰ does not represent amino or C₁₋₆ alkylamino;

provided also that, when R¹⁰ represents hydrogen, one of R¹² to R¹⁵ represents methylthio or methylsulphonyl or one or two of R¹² to R¹⁵ represent C₁₋₄ alkyl, C₁₋₄ alkoxy or halogen, and the remainder of the substituents R¹² to R¹⁵ represent hydrogen, then R¹¹ does not represent a 1H-tetrazol-5-yl group;

in association with one or more pharmaceutically acceptable carriers and/or excipients.

The invention also provides a compound of formula IA as defined above or a pharmaceutically acceptable salt thereof or a prodrug thereof for use in therapy.

Subject to the above provisos, the substituents R¹⁰ and R¹¹ to R¹⁵ in the compounds of formula IA correspond to the substituents R and R¹ to R⁵ respectively as defined with reference to the compounds of formula I.

Certain compounds falling within the definition of formula I above are novel. Accordingly, in a still further aspect the present invention provides a compound of formula IB or a salt or prodrug thereof:

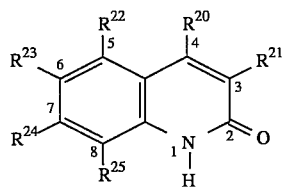

(IB)

wherein

R²⁰ represents a hydrogen atom, an amino group, a carboxy or C₂₋₆ alkoxycarbonyl group, or a group of formula -α-β-ε, in which α represents a chemical bond, an oxygen or sulphur atom, or an —NH— group;

β represents a carbonyl (C=O) or sulphonyl (SO₂) group, or a straight or branched alkylene chain containing from 1 to 6 carbon atoms; and ε represents C₁₋₆ alkyl, C₂₋₆ alkenyl, phenyl, —NR$^a$R$^b$, —CO₂R$^a$ or —CH₂CO₂R$^a$;

R²¹ is a group of part formula (i) or (ii):

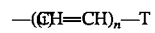

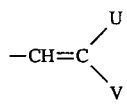

wherein

U and V independently represent cyano, carboxy, —COR⁶, —CO₂R⁶, —CO.SR⁶, —CONHOH or —CONHNH₂;

n is zero or 1, preferably zero;

T represents cyano, carboxy, —COR⁶, —CO₂R⁶, —CO.SR⁶, —CONHOH, —CONHNH₂ or a group of formula

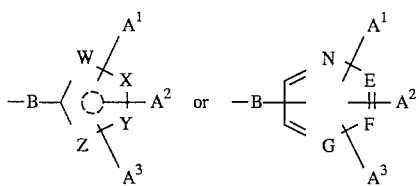

in which the broken circle represents two non-adjacent double bonds in any position in the five-membered ring;

B represents a bond or a carbonyl group (C=O);

W, X, Y and Z independently represent oxygen, sulphur, nitrogen or carbon, provided that no more than one of W, X, Y and Z represents oxygen or sulphur and at least one of W, X, Y and Z is other than carbon;

one of E, F and G represents nitrogen or carbon and the remainder represent carbon;

$A^1$, $A^2$ and $A^3$ represent one, two or three substituents not exceeding the maximum number permissible by the disposition of heteroatoms in the five- or six-membered ring, which substituents are independently selected from hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; or $A^1$ and $A^2$ or $A^2$ and $A^3$ together represent the residue of an aromatic or heteroaromatic ring;

one of $R^{22}$, $R^{23}$, $R^{24}$ and $R^{25}$ represents hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$, and the other three of $R^{22}$, $R^{23}$, $R^{24}$ and $R^{25}$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_aR^a$ or —$CONR^aR^b$; or $R^{22}$ and $R^{23}$, $R^{23}$ and $R^{24}$ or $R^{24}$ and $R^{25}$ together represent the residue of an aromatic or heteroaromatic ring;

$R^6$ represents hydrocarbon or a heterocyclic group; and $R^a$ and $R^b$ independently represent hydrogen, hydrocarbon or a heterocyclic group;

provided that, when $R^{21}$ represents carboxy or $C_{2-7}$ alkoxycarbonyl, one of the substituents $R^{22}$ to $R^{25}$ represents chloro or bromo and the other three substituents $R^{22}$ to $R^{25}$ are hydrogen, then $R^{20}$ does not represent amino or $C_{1-6}$ alkylamino;

provided also that, when $R^{20}$ represents hydrogen, one of $R^{22}$ to $R^{25}$ represents methylthio or methylsulphonyl or one or two of $R^{22}$ to $R^{25}$ represent $C_{1-4}$ alkyl, $C_{1-4}$ alkoxy or halogen, and the remainder of the substituents $R^{22}$ to $R^{25}$ represent hydrogen, then $R^{21}$ does not represent a 1H-tetrazol-5-yl group;

provided further that, when $R^{21}$ is ethoxycarbonyl, $R^{23}$ is nitro and $R^{22}$, $R^{24}$ and $R^{25}$ each represents hydrogen, then $R^{21}$ does not represent amino.

Subject to the above provisos, the substituents $R^{20}$ and $R^{21}$ to $R^{25}$ in the compounds of formula IB correspond to the substituents R and $R^1$ to $R^5$ respectively as defined with reference to the compounds of formula I.

Representative values of $R^{21}$ include cyano, carboxy, cyclopropylcarbonyl, benzylcarbonyl, thienylvinylcarbonyl, methoxycarbonyl, ethoxycarbonyl, phenylthio-ethoxycarbonyl, propoxycarbonyl, allyloxycarbonyl, hydroxyphenyl-ethoxycarbonyl, bis(methoxymethoxy)phenyl-ethoxycarbonyl, (t-butoxycarbonylaminomethyl)phenyl-ethoxycarbonyl, hydroxyphenyl-propoxycarbonyl, hydroxyphenylbutoxycarbonyl, methoxyphenyl-propenyloxycarbonyl, hydroxyphenyl-propynyloxycarbonyl, methoxyphenylpropynyloxycarbonyl, thienyl-ethoxycarbonyl, indolylethoxycarbonyl, methoxyindolyl-ethoxycarbonyl, indolylpropoxycarbonyl, phenethylthio-carbonyl, hydroxyaminocarbonyl, hydrazinocarbonyl, furyl, methylfuryl, ethylfuryl, isopropylfuryl, phenylfuryl, benzofuryl, thienyl, methylthienyl, benzylthienyl, benzothienyl, N-methylpyrrolyl, benzoyl-(N-methyl)pyrrolyl, methyloxadiazolyl, tetrazolyl, furoyl, methylfuroyl, dimethylfuroyl, benzofuroyl, nitrobenzofuroyl, thienoyl, methylthienoyl, bromothienoyl, dimethylthienoyl, benzothienoyl, N-methylpyrrolylcarbonyl, N-methylindolyl-carbonyl, pyridyl and ethoxycarbonyl-ethenyl. Particular values of $R^{21}$ are carboxy and tetrazolyl.

For use in medicine, the salts of the compounds of formula IB will be non-toxic pharmaceutically acceptable salts. Other salts may, however, be useful in the preparation of the compounds according to the invention or of their non-toxic pharmaceutically acceptable salts.

Suitable pharmaceutically acceptable salts of the compounds of formulae I, IA and IB above include alkali metal salts, e.g. sodium or potassium salts; alkaline earth metal salts, e.g. calcium or magnesium salts; and salts formed with suitable organic ligands, e.g. quaternary ammonium salts. Where appropriate, acid addition salts may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, citric acid, tartaric acid, carbonic acid or phosphoric acid.

The present invention includes within its scope prodrugs of the compounds of formulae I, IA and IB above. In general, such prodrugs will be functional derivatives of the compounds of formulae I, IA and IB which are readily convertible in vivo into the required compound. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

One sub-class of compounds according to the invention is represented by the compounds of formula IIA, and salts and prodrugs thereof:

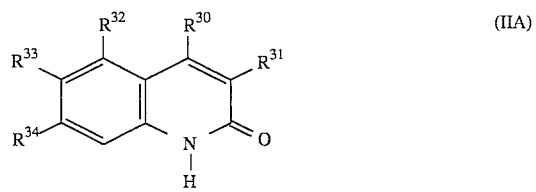

wherein $R^{30}$ represents a hydrogen atom, a carboxy group, or a group of formula $\alpha^1$-$\beta^1$—$\epsilon^1$, which $\alpha^1$ represents a chemical bond, an oxygen atom or an —NH— group;

$\beta^1$ represents a carbonyl (C=O) or sulphonyl (SO$_2$) group, or a group of formula —(CH$_2$)$_p$— in which p is 1, 2, 3 or 4; and $\epsilon^1$ represents amino, C$_{1-6}$ alkylamino, di(C$_{1-6}$)alkylamino, carboxy, C$_{2-6}$ alkoxycarbonyl, carboxymethyl or C$_{2-6}$ alkoxycarbonylmethyl;

R$^{31}$ represents carboxy, —COR$^{36}$ or —CO$_2$R$^{36}$;

R$^{32}$ represents hydrogen, halogen, cyano, trifluoromethyl, nitro, hydroxy, amino, carboxy, C$_{1-6}$ alkyl, C$_{2-6}$ alkenyl, C$_{1-6}$ alkoxy, C$_{1-6}$ alkylthio or C$_{2-6}$ alkoxycarbonyl;

R$^{33}$ represents hydrogen or halogen;

R$^{34}$ represents halogen, cyano, trifluoromethyl, nitro, hydroxy, amino, carboxy, C$_{1-6}$ alkyl, C$_{2-6}$ alkenyl, C$_{1-6}$ alkoxy, C$_{1-6}$ alkylthio or C$_{2-6}$ alkoxycarbonyl; and R$^{36}$ represents C$_{1-6}$ alkyl, C$_{3-7}$ cycloalkyl, aryl (C$_{1-6}$) alkyl, aryl (C$_{2-6}$) alkenyl, aryl (C$_{1-6}$) alkynyl, heteroaryl (C$_{1-6}$) alkyl or heteroaryl (C$_{2-6}$) alkenyl, any of which groups may be optionally substituted.

Particular examples of the substituent R$^{30}$ with reference to formula IIA above include hydrogen, carboxy, carboxymethyl, methoxycarbonyl-methyl, carboxymethoxy, methoxycarbonyl-methoxy, dimethylamino-ethylamino, dimethylamino-propylamino, carboxymethyl-carbonylamino, carboxy-carbonylamino and methoxycarbonyl-carbonylamino.

Examples of optional substituents on the group R$^{36}$ suitably include hydroxy, C$_{1-6}$ alkoxy, C$_{1-6}$ alkox(C$_{1-6}$) alkoxy and C$_{1-6}$ alkoxycarbonylamino (C$_{1-6}$) alkyl, especially hydroxy, methoxy, methoxymethoxy and t-butoxycarbonylaminomethyl.

Particular values of R$^{36}$ with respect to formula IIA include methyl, ethyl, n-propyl, cyclopropyl, benzyl, phenethyl, hydroxyphenethyl, bis(methoxymethoxy)phenethyl, (t-butoxycarbonylaminomethyl)-phenethyl, phenylpropyl, hydroxyphenylpropyl, phenylbutyl, hydroxyphenylbutyl, phenylallyl, methoxyphenylallyl, phenylpropargyl, hydroxyphenylpropargyl, methoxyphenylpropargyl, indolylethyl, methoxyindolylethyl, indolylpropyl, thienylethyl and thienylvinyl. A preferred group R$^{36}$ is cyclopropyl.

Suitably, R$^{32}$ represents hydrogen, nitro, methyl, ethyl, vinyl or halogen, especially chlorine or iodine. R$^{32}$ is hydrogen, ethyl or iodine. Preferably, Suitably, R$^{33}$ represents hydrogen or chlorine, preferably hydrogen.

Suitably, R$^{34}$ represents cyano, trifluoromethyl, nitro, methyl or halogen, preferably chlorine. Another sub-class of compounds according to the invention is represented by the compounds of formula IIB, and salts and prodrugs thereof:

(IIB)

wherein

R$^{40}$ represents a hydrogen atom, an amino group, a carboxy group, or a group of formula $\alpha^2$—$\beta^2$—$\epsilon^2$, in which $\alpha^2$ represents a chemical bond, an oxygen atom or an —NH— group;

$\beta^2$ represents a carbonyl (C=O) or sulphonyl (SO$_2$) group, or a group of formula —(CH$_2$)$_q$— in which q is 1, 2, 3 or 4; and $\epsilon^2$ represents C$_{1-6}$ alkyl, C$_{2-6}$ alkenyl, phenyl, amino, C$_{1-6}$ alkylamino, di(C$_{1-6}$)alkylamino, carboxy, C$_{2-6}$ alkoxycarbonyl, carboxymethyl or C$_{2-6}$ alkoxycarbonylmethyl;

A$^{11}$ represents C$_{1-6}$ alkyl; C$_{2-6}$ alkenyl, C$_{2-6}$ alkynyl, C$_{3-7}$ cycloalkyl, C$_{3-7}$ cycloalkyl(C$_{1-6}$)alkyl, aryl or aryl(C$_{1-6}$)alkyl;

B represents a bond or a carbonyl group (C=O);

R$^{42}$ represents hydrogen, halogen, cyano, trifluoromethyl, nitro, hydroxy, amino, carboxy, C$_{1-6}$ alkyl, C$_{2-6}$ alkenyl, C$_{1-6}$ alkoxy, C$_{1-6}$ alkylthio or C$_{2-6}$ alkoxycarbonyl;

R$^{43}$ represents hydrogen or halogen; and

R$^{44}$ represents halogen, cyano, trifluoromethyl, nitro, hydroxy, amino, carboxy, C$_{1-6}$ alkyl, C$_{2-6}$ alkenyl, C$_{1-6}$ alkoxy, C$_{1-6}$ alkylthio or C$_{2-6}$ alkoxycarbonyl.

Particular examples of the substituent R$^{40}$ with reference to formula IIB include hydrogen, amino, carboxy, carboxymethyl, methoxycarbonyl-methyl, carboxymethoxy, methoxycarbonyl-methoxy, allyloxy, benzylamino, dimethylamino-ethylamino, dimethylaminopropylamino, acetylamino, carboxymethyl-carbonylamino, carboxy-carbonylamino, methoxycarbonyl-carbonylamino, methylsulphonylamino and phenylsulphonylamino.

Examples of suitable values for the group A$^{11}$ include methyl, ethyl, isopropyl, vinyl, allyl, cyclopropyl, cyclopropylmethyl, phenyl and benzyl.

Suitably, R$^{42}$ represents hydrogen, nitro, methyl, ethyl, vinyl or halogen, especially chlorine or iodine. Preferably R$^{42}$ is hydrogen, ethyl or iodine.

Suitably, R$^{43}$ represents hydrogen or chlorine, preferably hydrogen.

Suitably, R$^{44}$ represents cyano, trifluoromethyl, nitro, methyl or halogen, preferably chlorine.

Specific compounds within the scope of the present invention include:

3-carboxy-7-chloro-2(1H)-quinolone;

and salts and prodrugs thereof.

In addition, the following compounds (each of which is referred to hereinafter as a "previously undisclosed compound of formula I") are not specifically disclosed in the prior art, and are therefore novel compounds according to the present invention:

4-amino-3-carboxy-7-chloro-2(1H)-quinolone;

7-chloro-3-(1H-tetrazol-5-yl)-2(1H)-quinolone;

and salts and prodrugs thereof.

The present invention also provides a pharmaceutical composition comprising a "previously undisclosed compound of formula I" as defined above or a pharmaceutically acceptable salt thereof or a prodrug thereof in association with one or more pharmaceutically acceptable carriers and/or excipients.

The present invention further provides a "previously undisclosed compound of formula I" or a pharmaceutically acceptable salt thereof or a prodrug thereof for use in therapy.

The pharmaceutical compositions of this invention are preferably in unit dosage forms such as tablets, pills, capsules, powders, granules, sterile parenteral solutions or suspensions, or suppositories, for oral, parenteral or rectal administration. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurodegeneration, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day. In a particular embodiment, the compounds may be conveniently administered by intravenous infusion.

The compounds of formula I above wherein R represents hydrogen, amino or a group of formula —α—β—ε in which α represents a chemical bond and β is a straight or branched alkylene chain containing from 1 to 6 carbon atoms, including the novel compounds according to the invention, may be prepared by a process which comprises cyclising a compound of formula III:

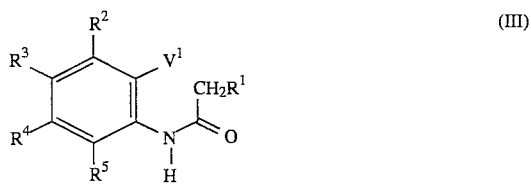

wherein $R^1$, $R^2$, $R^3$, $R^4$ and $R^5$ are as defined above; and $V^1$ represents an aldehyde (—CHO) or cyano (—CN) group, or a group of formula —CO—$β^a$—ε in which $β^a$ represents a straight or branched alkylene chain containing from 1 to 6 carbon atoms and ε is as defined above.

The reaction is conveniently carried out in the presence of a base, followed by a mild acidic work-up. Suitable bases of use in the reaction include sodium methoxide, sodium hydride and potassium hexamethyldisilazide.

When $V^1$ in the compounds of formula III above represents an aldehyde group, the product of the reaction is a compound of formula I wherein R is hydrogen. When $V^1$ represents a cyano group, the product of the reaction is a compound of formula I wherein R is an amino group. When $V^1$ represents a group of formula —CO—$β^a$—ε, the product of the reaction is a compound of formula I wherein R is a group of formula —α—β—ε in which α represents a chemical bond and β is a straight or branched alkylene group containing from 1 to 6 carbon atoms.

The compounds of formula I wherein R represents a group of formula —α—β—ε in which α represents a chemical bond, β is a methylene group and ε represents —$CO_2R^a$ may be prepared by intramolecular Michael cyclisation of a compound of formula IIIA:

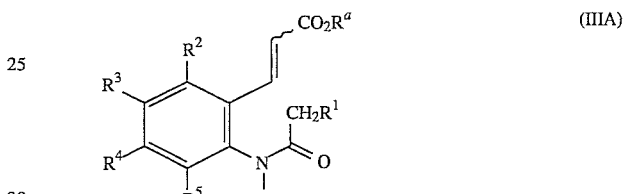

wherein $R^1$, $R^2$, $R^3$, $R^4$, $R^5$ and $R^a$ are as defined above; in the presence of a strong base, e.g. sodium methoxide; followed by quenching with a selenyl halide reagent, e.g. phenylselenyl chloride; and subsequent elimination of selenium to afford the double bond in the 3,4-position.

The intermediates of formulae III and IIIA above may conveniently be prepared by reacting a compound of formula $Q^1$—$CH_2$—$R^1$ with a compound of formula IV:

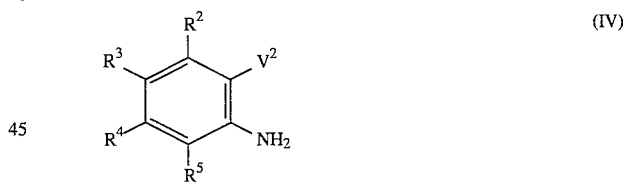

wherein $R^1$, $R^2$, $R^3$, $R^4$ and $R^5$ are as defined above; $V^2$ corresponds to the group $V^1$ as defined above or represents a group of formula —CH=CH.$CO_2R^a$ in which $R^a$ is as defined above; and $Q^1$ represents a reactive carboxylate moiety.

The reaction is conveniently effected in dichloromethane at room temperature or in 1,2-dichloroethane at reflux temperature, advantageously in the presence of a mild organic base such as triethylamine and/or 4-dimethylaminopyridine.

Suitable values for the reactive carboxylate moiety $Q^1$ include esters, for example $C_{1-4}$ alkyl esters; acid anhydrides, for example mixed anhydrides with $C_{1-4}$ alkanoic acids; acid halides, for example acid chlorides; orthoesters; and primary, secondary and tertiary amides.

Preferably, the group $Q^1$ is an acid halide group, in particular an acid chloride group. An alternative preferred species of formula $Q^1$—$CH_2$—$R^1$ is the activated ester derivative formed upon reaction of the carboxy compound $HO_2C$—$CH_2$—$R^1$ with bis(2-oxo-3-oxazolidinyl)phosphinic chloride (BOP-Cl).

The compounds of formula I wherein R represents a carboxy group, including the novel compounds according to the invention, may be prepared by a process which comprises reacting a compound of formula $HO_2C—CH_2—R^1$ with a compound of formula V:

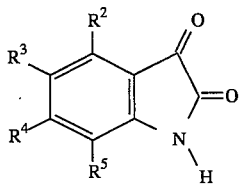

wherein $R^1$, $R^2$, $R^3$, $R^4$ and $R^5$ are as defined above

The reaction is conveniently carried out in the presence of sodium acetate at an elevated temperature, e.g. 200° to 230° C., by analogy with the methodology described, for example, in *J. Heterocycl. Chem.*, 1989, 26, 281.

The compounds of formula I wherein R represents a group of formula —α—β—ε in which α represents an oxygen or sulphur atom or an —NH— group, including the novel compounds according to the invention, may be prepared by reacting a compound of formula L-β—ε with a compound of formula VI:

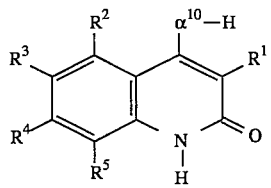

wherein $R^1$, $R^2$, $R^3$, $R^4$, $R^5$, β and ε are as defined above; $α^{10}$ represents an oxygen or sulphur atom or an —NH— group; and L represents a leaving group such as a halogen atom, e.g. chloro or bromo.

The reaction is conveniently carried out in the presence of a base. When $α^{10}$ represents oxygen or sulphur, a mild base such as sodium bicarbonate is advantageously employed, and the reaction is suitably effected in a solvent such as N,N-dimethylformamide. When $α^{10}$ represents an —NH— group, a preferred base, depending upon the nature of the reagent L—β—ε, is sodium hydride or potassium hexamethyldisilazide, and the reaction is advantageously effected in a compatible solvent, such as tetrahydrofuran.

In an alternative process, the compounds of formula I wherein R represents a group of formula —α—β—ε in which α represents an —NH— group, including the novel compounds according to the invention, may be prepared by reacting a compound of formula $H_2N$—β—ε, wherein β and ε are as defined above, with a compound of formula VI above wherein $α^{10}$ represents an oxygen atom.

The reaction is conveniently effected by heating the reagents together at the reflux temperature of the mixture, by analogy with the methodology described, for example, in *Vestn. Slov, Kem. Drus.*, 1986, 33, 271; or, if necessary, by maintaining the reaction mixture at an elevated temperature for several days in a sealed tube.

A given intermediate of formula VI above wherein $α^{10}$ represents sulphur may be prepared from the corresponding compound of formula VI wherein $α^{10}$ represents oxygen by treating the latter compound firstly with N,N-dimethylthiocarbamyl chloride and then with a mineral acid such as hydrochloric acid, followed by hydrolysis with base, e.g. sodium hydroxide, by analogy with the procedure described in WO-A-91/01973.

The intermediates of formula VI above wherein $α^{10}$ represents oxygen may be prepared by the procedures described in EP-A-0459561 or by methods analogous thereto. Additional sources of reference for preparing compounds corresponding to those of formula VI above wherein $α^{10}$ represents oxygen include, for example, *J. Org. Chem.*, 1976, 41, 825.

The aromatic intermediates of formulae IV and V above, as well as the intermediates of formula $HO_2C$—$CH_2$—$R^1$ and $Q^1$—$^{CH}{}_2$—$R^1$ where they are not commercially available, may be prepared by the methods described in the accompanying Examples, or by methods analogous thereto which will be readily apparent to those skilled in the art.

As will be appreciated, the compounds of formula VI above wherein $α^{10}$ represents an —NH— group, which can be used as intermediates in the preparation of compounds in accordance with the present invention, are themselves compounds according to the invention. It is to be understood that any compound of formula I, IA or IB initially obtained from any of the above processes may, where appropriate, subsequently be elaborated into a further desired compound of formula I, IA or IB respectively using techniques known from the art.

For example, a compound of formula I initially obtained wherein R is carboxy may be converted into a corresponding compound of formula I wherein R represents a $C_{1-6}$ alkoxycarbonyl group by standard esterification procedures common in the art.

Moreover, a compound of formula I initially obtained wherein $R^1$ represents a group of formula —$CO_2R^6$ may subsequently be converted into the desired compound of formula I wherein $R^1$ represents a different group —$CO_2R^6$ by conventional transesterification procedures known from the art. For example, this transesterification can be brought about simply by heating the ester of formula I initially obtained, at a temperature in excess of 130° C., in an alcohol of formula $R^6OH$ in which $R^6$ represents the residue of the ester group —$CO_2R^6$ in the desired final product of formula I, the alcohol $R^6OH$ itself simultaneously serving as solvent.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (-)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wutts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently and selectively block responses to NMDA and/or AMPA in a brain slice from rat cortex, and inhibit the binding of agonists and antagonists to the strychnine-insensitive site present on the NMDA receptor and/or AMPA binding to rat forebrain membranes.

Cortical Slice Studies

The effects of compounds of the invention on responses to NMDA and AMPA were assessed using the rat cortical slice as described by Wong et al., *Proc. Natl. Acad. Sci. USA*, 1986, 83, 7104. The apparent equilibrium constant ($K_b$) was calculated from the righthand shift in the NMDA or AMPA concentration-response curves produced by the compound under test. Of those compounds of the accompanying Examples which were tested, all were found to possess a $K_b$ value in response to NMDA of below 150 µM.

Binding Studies

The ability of test compounds to displace $^3$H-L- 689,560 (trans-2-carboxy-5,7-dichloro-4-phenylaminocarbony-lamino- 1,2,3,4-tetrahydroquinoline) binding to the strychnine-insensitive glycine site present on the NMDA receptor of rat forebrain membranes was determined by the method of Grimwood et al., *Proceedings of The British Pharmacological Society*, July 1991, Abstract C78. The concentration of the compounds of the accompanying Examples required to displace 50% of the specific binding ($IC_{50}$) is below 50 µM in each case.

EXAMPLE 1

3-Carboxy-7-chloro-2(1H)-quinolone

A suspension of 2-amino-4-chlorobenzyl alcohol (8.4 g, 53 mmol) in $CH_2Cl_2$ (300 ml) was treated with methyl malonyl chloride (21.7 g), and the reaction stirred overnight at room temperature. The reaction was concentrated to a volume of 100 ml, diethyl ether added (300 ml), and filtered. The filtrate was evaporated in vacuo to leave an oil which was dissolved in ethyl acetate and washed several times with saturated sodium hydrogen carbonate, water, brine, dried and evaporated to give 11.9 g of the ester-amide.

A solution of the ester-amide (11.7 g) in methanol (150 ml) was stirred with potassium carbonate (2 g) for 24 h. The reaction was partitioned between water and ethyl acetate. The organic phase was separated, washed with brine, dried and evaporated. The residue was purified by chromatography (3.5% methanol-$CH_2Cl_2$ eluent) to give the benzyl alcohol (4.17 g); mp 66°–68° C.

The benzyl alcohol (2.4 g) was stirred with pyridinium chlorochromate (2.8 g) in $CH_2Cl_2$ (25 ml) for 2 h, diethyl ether was added and the reaction filtered through silica. The filtrate was evaporated in vacuo and recrystallised to give the aldehyde (2.2 g); mp 77°–78° C. (propan-2-ol).

The aldehyde (106mg) was dissolved in methanol (2 ml) and treated with sodium methoxide (54 mg) for 1.5 h.

Ethyl acetate was added to the reaction and the suspension washed with dil. HCl, water and evaporated in vacuo to give the quinolone methyl ester (92 mg).

A solution of the methyl ester (371 mg, 1.56 mmol) in 15 ml THF was hydrolysed using lithium hydroxide (3.2 ml, 1M solution). After 2 h, the reaction was acidified (1N HCl), evaporated and the residue stirred with 20 ml water for 1 h. The solid was collected by filtration, washed with methanol, diethyl ether and dried to give 251 mg of the title compound as a white solid. mp 317°–318° C. (DMF-water); (Found: C, 53.19; H, 2.78; N, 6.08. $C_{10}H_6NO_3Cl+0.1H_2O$ requires C, 53.28; H, 2.77; N, 6.21%); δ (360 MHz, DMSO-$d_6$) 7.45 (1H, dd, J=2.0 and 8.5 Hz, H-6), 7.50 (1H, d, J=2.0 Hz, H-8), 8.07 (1H, d, J=8.5 Hz, H-5), 8.96 (1H, s, H-4), 13.1 (1H, br s), 14.4 (1H, br s); m/z (EI$^+$) 223 (M+).

EXAMPLE 2

7-Chloro-3-(5-tetrazole)-2(1H)-quinolone

2-Amino-4-chlorobenzyl alcohol (3 g, 19.29 mmol) and cyanoacetic acid (3.61 g, 42.44 mmol) were reacted in a similar manner as described in Example 1 to give 0.63 g of 7-chloro-3-cyano- 2(1H)-quinolone. mp 306°–309° C. This nitrile (0.46 g) was dissolved in 1-methylpyrrolidinone and treated with triethylammonium hydrochloride (0.465 g) and sodium azide (0.44 g). The reaction was heated to 140° C. for 1 h, cooled, acidified (HCl), and extracted with ethyl acetate (2×). The combined organic phases were extracted into dilute sodium hydroxide (2×) and washed with diethyl ether. The aqueous layer was acidified and the precipitate which formed was extracted into ethyl acetate (3×). The combined organic phases were washed with water and then evaporated to give the title compound as a powdered brown solid; mp 327° C. (dec) (DMF, acetone, water). (Found: C, 48.61; H, 2.47. $C_{10}H_6ClN_5O$ requires C, 48.50; H, 2.44%); $δ_H$ (360 MHz, DMSO-$d_6$) 7.36 (1H, d, dd, J=8.4 and 2.0 Hz, 6-H), 7.44 (1H, d, J=2.0 Hz), 8.01 (1H, d, J=8.4 Hz, 5-H), 8.98 (1H, s, 4-H), 12.3–12.7 (1H, vbr s, NH); m/z (EI$^+$) 247 (M+).

EXAMPLE 3

4-Amino-3-carboxy-7-chloro-2(1H)-quinolone

5-Chloro anthranilonitrile (1.3 g) and methyl malonyl chloride (0.87 ml) was heated at reflux for 14 h in 1,2-dichloroethane (150 ml). The reaction mixture was concentrated in vacuo and the residue was triturated with methanol to give an intermediate amide.

The amide was dissolved in DMF (20 ml) and treated with sodium hydride (0.492 g, 80% disp. in oil). The reaction was heated at 100° C. for 3.5 h, cooled and poured into water (100 ml). The reaction was acidified to pH1 (1N HCl), and a solid was collected by filtration to give the title compound, 87 mg (mp> 330° C. (DMF-water)). 8 (360 MHz, DMSO-d6), 7.38 (2H, m, 6-H and 8-H), 8.27 (1H, d, J=9.4Hz, 5-H), 8.51 (1H, br s, $NH_AH_B$), 9.88 (1H, br s, $NH_AH_B$), 11.97 (1H, br s, NH), 15.84 (1H, s, $CO_2$H); m/z (CI$^-$) 238 (M+). Found: C, 48.49; H, 3.13; N, 11.07. $C_{10}H_7ClN_2O_3 \cdot 0.5H_2O$ requires C, 48.50; H, 3.26, N. 11.31%.

Tablet Preparation

Tablets containing 1.0, 2.0, 25.0, 26.0, 50.0 and 100.0 mg, respectively of the following compounds are prepared as illustrated below:

3-Carboxy-7-chloro-2(1H)-quinolone
7-Chloro-3-(5-tetrazole)-2(1H)-quinoline

4-Amino-3-carboxy-7-chloro-2(1H)-quinolone

| | Amount-mg | | |
|---|---|---|---|
| TABLE FOR DOSES CONTAINING FROM 1–25 MG OF THE ACTIVE COMPOUND | | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |
| TABLE FOR DOSES CONTAINING FROM 26–100 MG OF THE ACTIVE COMPOUND | | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

We claim:

1. A method for the treatment of conditions which require the administration of a selective non-competitive antagonist of NMDA receptors, which comprises administering to a patient in need of such treatment an effective amount of a compound of formula I or a pharmaceutically acceptable salt thereof or a prodrug thereof:

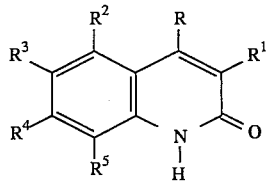

wherein:

R represents a hydrogen atom or an amino group, $R^1$ is carboxy or tetrazolyl, one of $R^2$, $R^3$, $R^4$ and $R^5$ represents halogen, and the other three of $R^2$, $R^3$, $R^4$ and $R^5$ independently represent hydrogen or halogen.

2. A pharmaceutical composition comprising a compound of formula IA or a pharmaceutically acceptable salt thereof or a prodrug thereof:

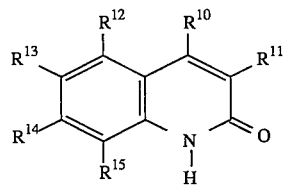

wherein:

$R^{10}$ represents a hydrogen atom or an amino group, $R^{11}$ is carboxy or tetrazolyl, one of $R^{12}$, $R^{13}$, $R^{14}$ and $R^{15}$ represents halogen, and the other three of $R^{12}$, $R^{13}$, $R^{14}$ and $R^{15}$ independently represent hydrogen or halogen;

provided that, when $R^{11}$ represents carboxy, one of the substituents $R^{12}$ to $R^{15}$ represents chloro or bromo and the other three substituents $R^{12}$ to $R^{15}$ are hydrogen, then $R^{10}$ does not represent amino;

provided also that, when $R^{10}$ represents hydrogen, one or two of $R^{12}$ to $R^{15}$ represent halogen, and the remainder of the substituents $R^{12}$ to $R^{15}$ represent hydrogen, then $R^{11}$ does not represent a $^1$H-tetrazol-5-yl group;

in association with one or more pharmaceutically acceptable carriers and/or excipients.

3. A compound of formula IB or a pharmaceutically acceptable salt or prodrug thereof:

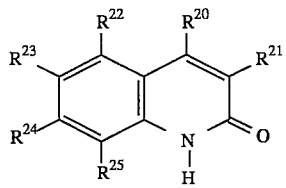

wherein:

$R^{20}$ represents a hydrogen atom or an amino group, $R^{21}$ is carboxy or tetrazolyl, one of $R^{22}$, $R^{23}$, $R^{24}$ and $R^{25}$ represents halogen, and the other three of $R^{22}$, $R^{23}$, $R^{24}$ and $R^{25}$ independently represent hydrogen or halogen;

provided that, when $R^{21}$ represents carboxy, one of the substituents $R^{22}$ to $R^{25}$ represents chloro or bromo and the other three substituents $R^{22}$ to $R^{25}$ are hydrogen, then $R^{20}$ does not represent amino;

provided also that, when $R^{20}$ represents hydrogen, one or two of $R^{22}$ to $R^{25}$ represent halogen, and the remainder of the substituents $R^{22}$ to $R^{25}$ represent hydrogen, then $R^{21}$ does not represent a 1 H-tetrazol-5-yl group.

4. A compound as claimed in claim 3 represented by formula IIA, and pharmaceutically acceptable salts and prodrugs thereof:

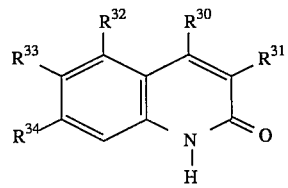

wherein:

$R^{30}$ is a hydrogen atom, $R^{31}$ is carboxy, $R^{32}$ represents hydrogen or halogen;

$R^{33}$ represents hydrogen or halogen; and $R^{34}$ represents halogen.

5. A method for the treatment and/or prevention of conditions which require the administration of an antagonist of AMPA receptors, which comprises administering to a patient in need of such treatment an effective amount of a compound of formula I as defined in claim 1 or a pharmaceutically acceptable salt thereof or a prodrug thereof.

6. A compound as claimed in claim 3 selected from:

3-carboxy-7-chloro-2(1H)-quinolone;
and salts and prodrugs thereof.

7. A compound selected from:

4-amino-3-carboxy-7-chloro-2(1H)-quinolone;

7-chloro-3-(1H-tetrazol-5-yl)-2(1H)-quinolone; and salts and prodrugs thereof.

8. A pharmaceutical composition comprising a compound as claimed in claim 6 or a pharmaceutically acceptable salt thereof or a prodrug thereof in association with one or more pharmaceutically acceptable carriers and/or excipients.

* * * * *